United States Patent
Reyes et al.

(10) Patent No.: US 11,395,763 B2
(45) Date of Patent: Jul. 26, 2022

(54) VITRECTOMY PROBE INTERFACING COMPONENT

(71) Applicant: Alcon Inc., Fribourg (CH)

(72) Inventors: Nathaniel Reyes, Santa Anna, CA (US); John R. Underwood, Laguna Nigel, CA (US)

(73) Assignee: Alcon Inc., Fribourg (CH)

( * ) Notice: Subject to any disclaimer, the term of this patent is extended or adjusted under 35 U.S.C. 154(b) by 236 days.

(21) Appl. No.: 16/883,012

(22) Filed: May 26, 2020

(65) Prior Publication Data

US 2020/0375796 A1    Dec. 3, 2020

Related U.S. Application Data

(60) Provisional application No. 62/853,880, filed on May 29, 2019.

(51) Int. Cl.
    *A61F 9/007*      (2006.01)

(52) U.S. Cl.
CPC ...... *A61F 9/00745* (2013.01); *A61F 9/00727* (2013.01); *A61F 9/00763* (2013.01)

(58) Field of Classification Search
CPC ...... A61B 17/320016; A61B 17/32002; A61B 17/320068; A61B 2017/320024; A61B 2017/320028; A61B 2017/320032; A61B 2017/320082; A61B 2017/320088; A61B 2017/320089; A61B 2017/320098; A61F 9/00745; A61F 9/00727; A61F 9/00763; A61F 2250/0075; A61F 2250/0093
See application file for complete search history.

(56) References Cited

U.S. PATENT DOCUMENTS

| | | | |
|---|---|---|---|
| 4,909,249 A | * | 3/1990 | Akkas ............. A61F 9/00763 606/171 |
| 8,038,692 B2 | | 10/2011 | Valencia |
| 8,888,802 B2 | | 11/2014 | Underwood |
| 9,962,226 B2 | | 5/2018 | Brennan |
| 10,143,588 B2 | | 12/2018 | Sussman |
| 10,251,782 B2 | | 4/2019 | Farley |
| 10,639,197 B2 | | 5/2020 | Lopez |

(Continued)

FOREIGN PATENT DOCUMENTS

| | | |
|---|---|---|
| EP | 0316085 A1 | 5/1989 |
| WO | 2011149748 A1 | 12/2011 |
| WO | 2020151908 A1 | 7/2020 |

OTHER PUBLICATIONS

Alcon Global Vitreoretinal Product Catalog, Feb. 2014, pp. 1-24.

*Primary Examiner* — Richard G Louis
*Assistant Examiner* — Chima U Igboko

(57) ABSTRACT

A unique vitrectomy probe with an interfacing component for attenuating vibrations during a vitrectomy procedure. The component may be of elastomeric construction tailored to attenuating the vibrations. Additionally, the component may strategically reside at an interface between the housing that accommodates moving parts of the probe and an ergonomic shell meant for resting at purlicue a surgeon's hand. In this way, vibrations are largely attenuated before reaching the shell and distracting the surgeon. Additionally, the shell, housing and interface are architecturally constructed for user-friendly shell removal for surgeons wishing to perform vitrectomy procedures in absence of the shell.

5 Claims, 6 Drawing Sheets

(56) References Cited

U.S. PATENT DOCUMENTS

2011/0295292 A1 12/2011 Hsia
2017/0172604 A1* 6/2017 Denham ............ A61B 17/3468
2020/0179102 A1 6/2020 Chen et al.

* cited by examiner

VITRECTOMY PROBE INTERFACING COMPONENT

PRIORITY CLAIM

This application claims the benefit of priority of U.S. Provisional Patent Application Ser. No. 62/853,880 titled "Vitrectomy Probe Interfacing Component", filed on May 29, 2019, whose inventors are Nathaniel Reyes and John R. Underwood, which is hereby incorporated by reference in its entirety as though fully and completely set forth herein.

BACKGROUND

Over the years, many dramatic advancements in the field of eye surgery have taken place. However, regardless of the particular procedure, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany cataract surgery, surgery to repair a retina, to address a macular pucker or a host of other issues.

The vitreous humor itself is a clear gel that may be removed by an elongated probe when inserted through a pre-placed cannula at the eye. More specifically, the probe includes a central channel for removal of the vitreous humor. Further, the cannula provides a structurally supportive conduit strategically located at an offset location at the front of the eye, such as the pars plana. In this way, the probe may be guidingly inserted into the eye in a manner that avoids damage to the patient's lens or cornea.

Unfortunately, removal of the vitreous humor requires greater care than simply applying a vacuum through the channel of the probe. This is because the vitreous humor includes a fibrous matrix of collagen fibrils. Therefore, merely applying a vacuum to the gel would place the surrounding eye structure in jeopardy. That is, the fibrous nature of the gel is such that a vacuum pull on the gel into the probe might translate into a pull on the retina, optic nerve or other delicate eye structures.

In order to address this issue, vitrectomy probes are configured to cut vitreous humor as it is drawn into the channel of the probe. In this way, a continuous fibrous pull on the gel-like substance does not translate into a pull on delicate eye structures. Instead, the vitreous humor is pulled into the channel of the probe in very small, chopped segments. This chipping or cutting of the vitreous humor occurs by the reciprocation of a cutter within the channel of the probe. More specifically, the cutter reciprocates back and forth at a port for intake of the vitreous humor in a manner that cuts the substance as it is being drawn into the channel. Perhaps 5,000 to 10,000 cuts per minute (or more) may take place in this manner in order to safeguard the eye from pulling by the vitreous humor as it is being removed.

Of course, reciprocating a cutter in this manner means that during the vitrectomy, vibrations are naturally translated through the vitrectomy probe. Therefore, the surgeon that is manually carrying out the procedure faces the prospect of a vibration related distraction while manipulating the probe in tight delicate spaces.

In addition to vibration related distraction, the probe is generally outfitted with an extended handle or shell that supportively rests at the purlicue at the base of the surgeon's index finger close to the thumb during a vitrectomy. This is perhaps similar to how the extended end of a pencil would rest during writing. However, unlike writing, the precise delicate nature of a vitrectomy is such that some surgeons prefer holding the probe without utilizing the shell during the procedure. That is, surgeons have been known to pry the shell off the probe in a manner that allows for more fine control over the probe, much like manipulating a sewing needle in contrast to a long pencil. Prior art probes have a tight interference/friction fit between the shell and the probe that requires a large force to pull the shell off the probe. The outer part of the prior art shell would be forced outward when pulled off the probe because the outer part would slide over a protruding portion on a probe outer circumference. To inhibit accidental removal, the interfering geometry between the probe outer circumference and shell required the shell to be pried, wiggled, and/or twisted off to cause enough outer deformation on the shell to be pulled off the probe. Of course, crudely prying the end off a surgical tool in advance of eye surgery is problematic. Even for the surgeon that might be adept at shell removal without damaging the tool, a certain amount of user friendliness appears to be lacking.

SUMMARY

A vitrectomy probe is disclosed. The probe includes a component housing for accommodating moving components to support a vitrectomy procedure. An ergonomic shell is physically coupled to the housing at discrete catch extension locations. Further, a securing interface between the shell and the housing is provided which substantially eliminates contact between the shell and the housing outside of the extension locations. In one embodiment, deflection of the catch extensions may be employed to remove the shell. In another, the interface is of an elastomeric construction for isolation of vibration from the housing during the procedure.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a procedure in which vitreous humor is removed to address vitreous hemorrhage is illustrated. However, tools and techniques detailed herein may be employed in a variety of other manners. For example, embodiments of a vitrectomy probe as detailed herein may be utilized to address retinal detachments, macular pucker, macular holes, vitreous floaters, diabetic retinopathy or a variety of other eye conditions. Regardless, so long as the vitrectomy probe incorporates an embodiment of an interfacing component to minimize contact between a housing and a shell of the probe, appreciable benefit may be realized.

Figure 1:
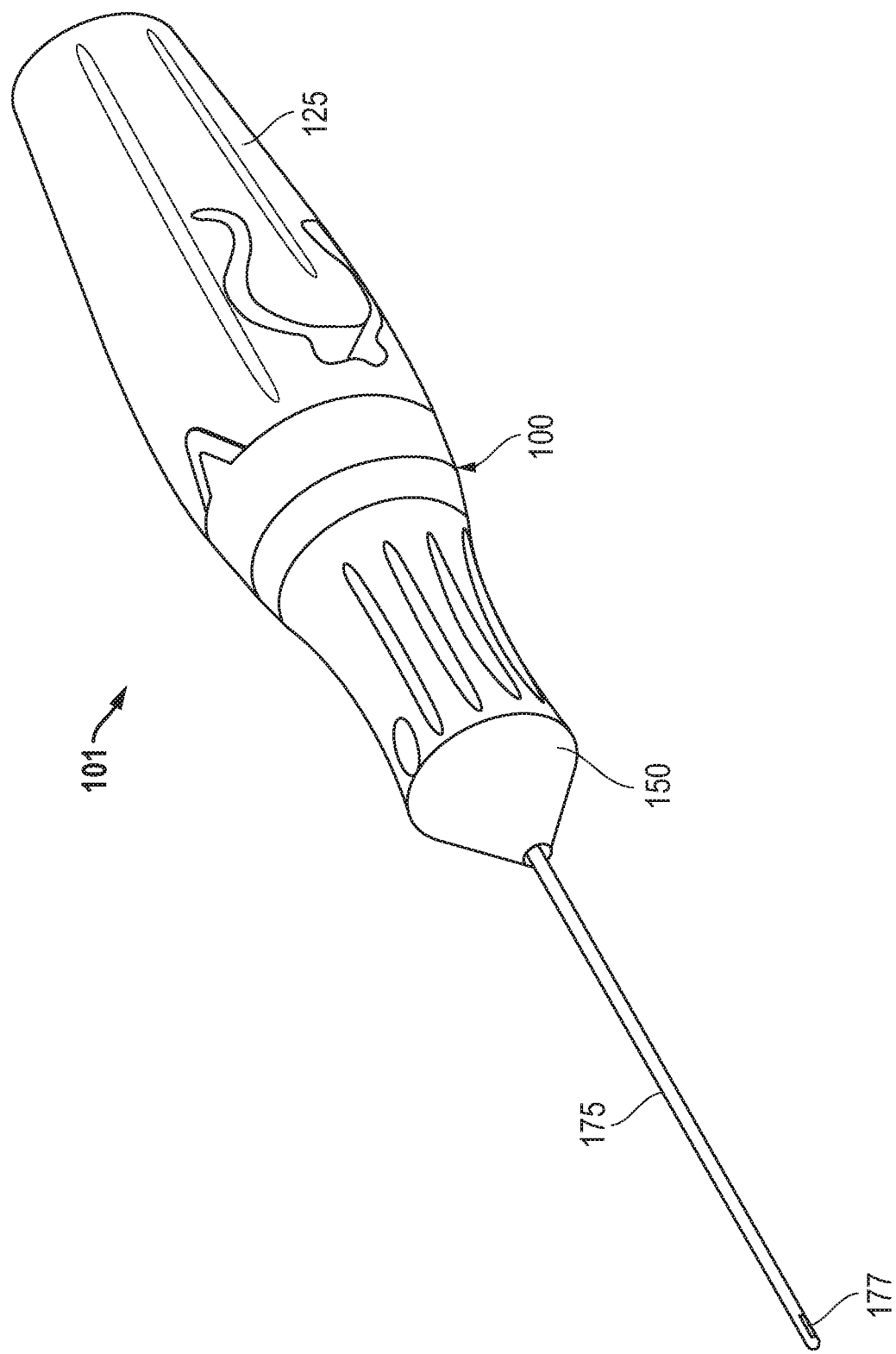
FIG. 1 is a perspective view of an embodiment of a vitrectomy probe utilizing a unique interfacing component.

Referring now to FIG. 1, a perspective view of an embodiment of a vitrectomy probe 101 is shown utilizing a unique interfacing component 100. This component 100 is positioned between a component housing 150 and a shell 125. In absence of the shell 125, the handheld portion of the probe 101 may include the housing that is generally under a few inches in total length. Therefore, the shell 125 is provided as a form of ergonomic support for the surgeon during a vitrectomy procedure.

As detailed further below, however, as a matter of user preference, some surgeons choose to utilize the probe 101 without the support of the shell 125. Therefore, in the embodiment shown, the shell 125 is removable, rather than providing the probe 101 to the surgeon in a monolithic form. Thus, surgeons who wish to remove the shell 125 may do so in a user-friendly manner and in a manner that does not subject the probe 101 to potential damage with the surgeon crudely attempting to pry the shell 125 from the probe 101. In this way, the vitrectomy procedure may be performed with the surgeon holding the housing 150 solely at the purlicue without any other interfering support.

Of course, the surgeon may more often prefer to leave the shell 125 in place for added support at the purlicue, like an extended pencil. Thus, the interfacing component 100 is configured to both stably accommodate securing of the shell 125 to the housing 150 during surgery while also facilitating a user friendly removal of the shell 125 if need be.

Stably accommodating the shell 125 during surgery means that the shell 125 may be subject to vibrations that are translated throughout the probe 101 during a procedure. More specifically, with added reference to FIG. 3, the needle 175 accommodates an internal reciprocating cutter that traverses a port 177 as vitreous humor is drawn there into. In this way, vitreous humor may be cut as it is taken up so as to avoid a fibrous pull on delicate part of the patient's eye 350. Reciprocating the cutter for this purpose means that moving components within the housing 150 subject the entire probe 101 to a certain degree of vibration.

In the embodiment shown, the interfacing component 100 may be tailored to mitigate the degree of vibration that is translated to the shell 125. That is, the component 100 is strategically located between the housing 150, which accommodates the moving components, and the shell 125. Thus, with the proper architecture and material selection, the majority of the vibrations from the moving components in the housing 150 may be attenuated by the interfacing component 100 before reaching the shell 125. Thus, potentially distracting vibrations to the surgeon may be avoided during a delicate eye surgery.

Figure 2:
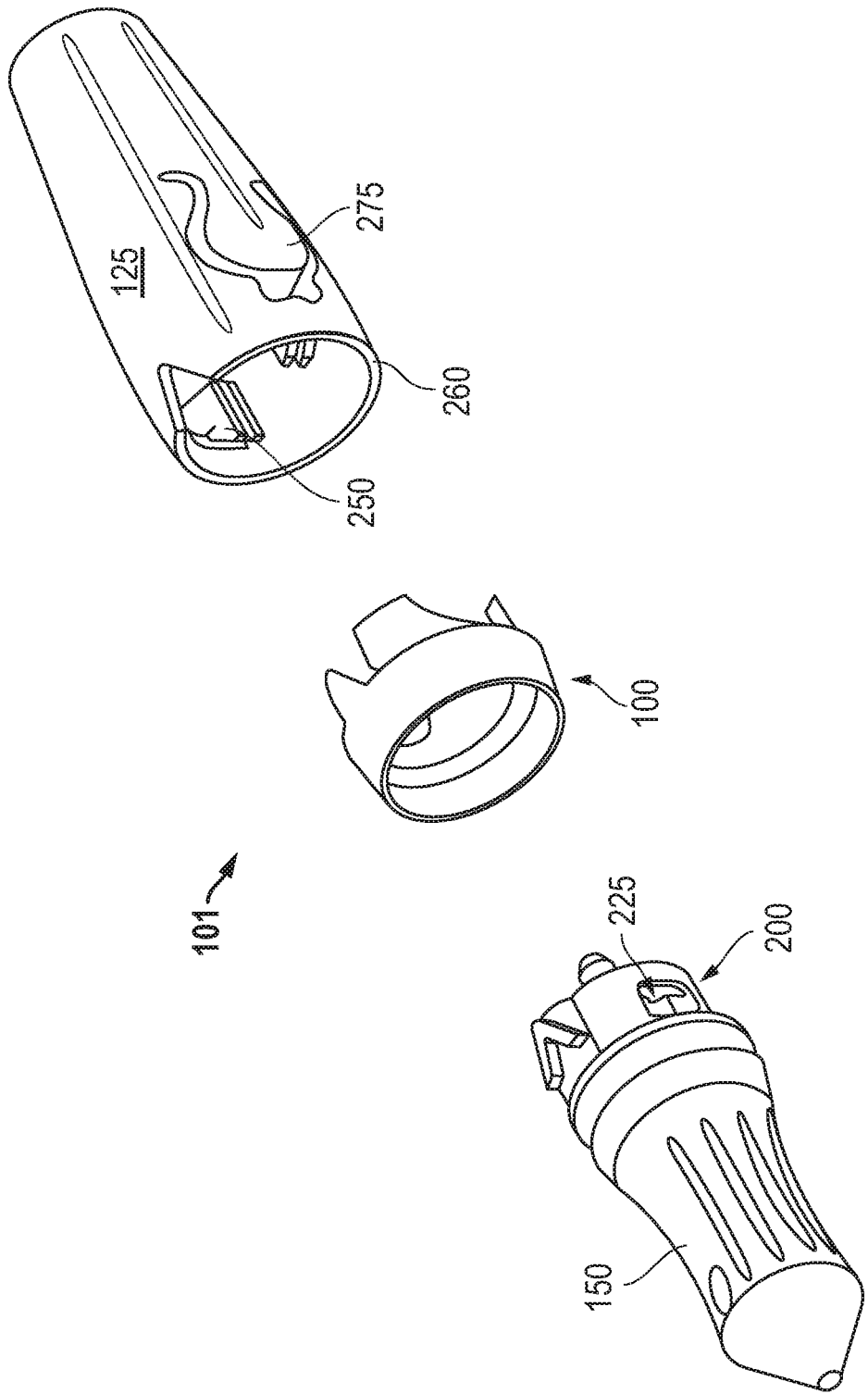
FIG. 2 is an exploded perspective view of the vitrectomy probe of FIG. 1 revealing how the interfacing component assembles relative other components of the probe.

Continuing with reference to FIG. 2, an exploded perspective view of the vitrectomy probe 101 of FIG. 1 is shown. In this view, the unique architecture of the interfacing component 100 is more apparent. Specifically, the component 100 is shaped to circumferentially interface and accommodate a leading edge 260 of the shell 125. Only catch extensions 250 at two discrete locations reach beyond the interfacing component 100 to reach the structure of the housing 150. Specifically, as illustrated, the extensions 250 may deflectingly secure the shell 125 to the component housing 150 through keyed orifices 225 at an internal housing 200 of the component housing 150.

The coupling of the extensions 250 at the orifices 225 limits the direct physical interaction between the shell 125 and the housings 150, 200 to these discrete points. All other physical interfacing at the leading edge 260 of the shell 125 is at and with the interfacing component 100. As detailed further below, the housings 150, 200 accommodate the moving parts of the probe 101. Therefore, limiting contact between the shell 125 and the housings 150, 200 to discrete locations as indicated, helps to minimize the translation of vibrations from the housings 150, 200 to the shell 125. Thus, the above noted potential for vibration distraction to the surgeon during an eye operation may also be minimized. Indeed, along these lines, the interfacing component 100 may be constructed of a conventional elastomeric polymer tailored to attenuate vibration.

The features of the interfacing component 100 described above are such that in one embodiment, the majority of vibrations from the vitrectomy probe 101 during operation do not reach the shell 125 when left in place by the surgeon. This is the case even where internal components of the probe 101 are moving rapidly enough to support over 5,000 cuts per minute as described above and further below. Of course, the shell 125 is also equipped with depressible tabs 275 at opposite sides from one another. Therefore, the surgeon may elect to pinch the tabs 275 toward one another to effectuate deflection of catch extensions 250 from the orifices 225 for removal of the shell 125 completely from the probe 101. In this way, for surgeons who choose this technique, vibration distraction via the shell 125 may be eliminated altogether.

By way of specific example, in one embodiment the interfacing component 100 circumferentially contacts over 300° of the leading edge 260 of the shell 125. At the same time, direct contact between the shell 125 and the housings 150, 200 is limited to the discrete locations of the extensions 250 at the orifices 225 which translates to an equivalent of under about 75°. In this manner, the architectural and material makeup of the interfacing component 100 may attenuate a majority of the vibrations emanating from the housings 200, 150 before they reach the shell 125 when it is left on the probe 101 during a surgical procedure.

Figure 3:
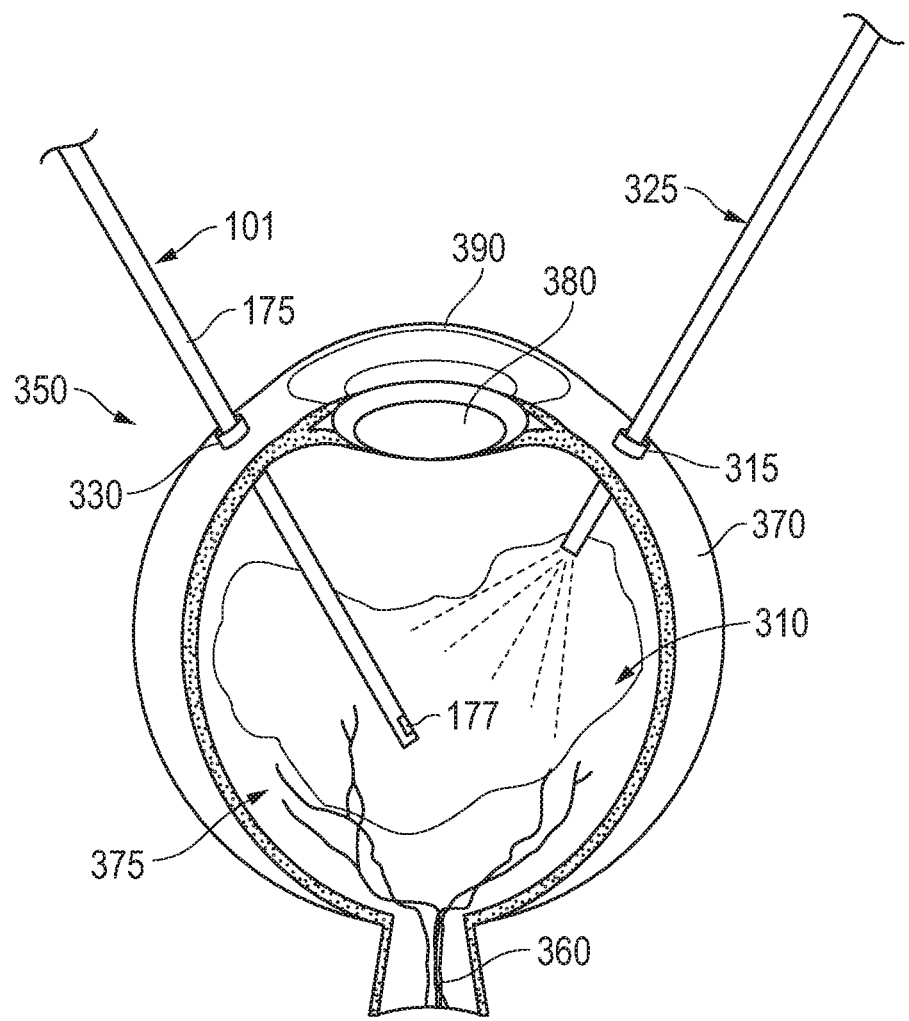
FIG. 3 is a side cross-sectional overview of a patient's eye during a vitrectomy procedure in which the vitrectomy probe of FIGS. 1 and 2 is utilized.

Referring now to FIG. 3, a side cross-sectional overview of a patient's eye 350 is shown during a vitrectomy procedure. During this surgical procedure, the vitrectomy probe 101 of FIGS. 1 and 2 is utilized. Specifically, the needle 175 is inserted through a preplaced cannula 330 and directed toward a region 310 where vitreous humor is to be removed. Specifically, as described above, a suction is applied and the port 177 is used for the uptake of the vitreous humor or other substances. For example, in the procedure illustrated, a hemorrhage may be taking place in the region 310 such that blood is drawn into the port 177 along with the vitreous humor.

As also described above, a cutter is reciprocating within the needle 175 during this delicate procedure. As described further below, this means that a diaphragm 450 is repeatedly striking internal structure of the housings 150, 200 of FIG. 2, likely in excess of 10,000 times per minute (see FIGS. 4A and 4B). Therefore, a notable amount of vibrations is prone to propagate through the probe 101 during a delicate eye surgery. However, due to the interfacing component 100 detailed above, a majority of this vibration may fail to reach the shell 125 in the surgeons hand at this critical time (see FIGS. 1 and 2).

Continuing with reference to FIG. 3, the surgery illustrated includes the probe 101 and a light instrument 325 reaching into the eye 350 through cannulas 315, 330 positioned in an offset manner at the sclera 370. In this way, the more delicate cornea 390 and lens 380 may be avoided. By the same token, the optic nerve 360 and retina 375 are also quite delicate. Therefore, given that the needle 175 is capable of reaching these delicate features at the back of the eye 350, the minimizing of potential distracting vibrations to the surgeon as described herein may be of substantial benefit.

Figure 4A:
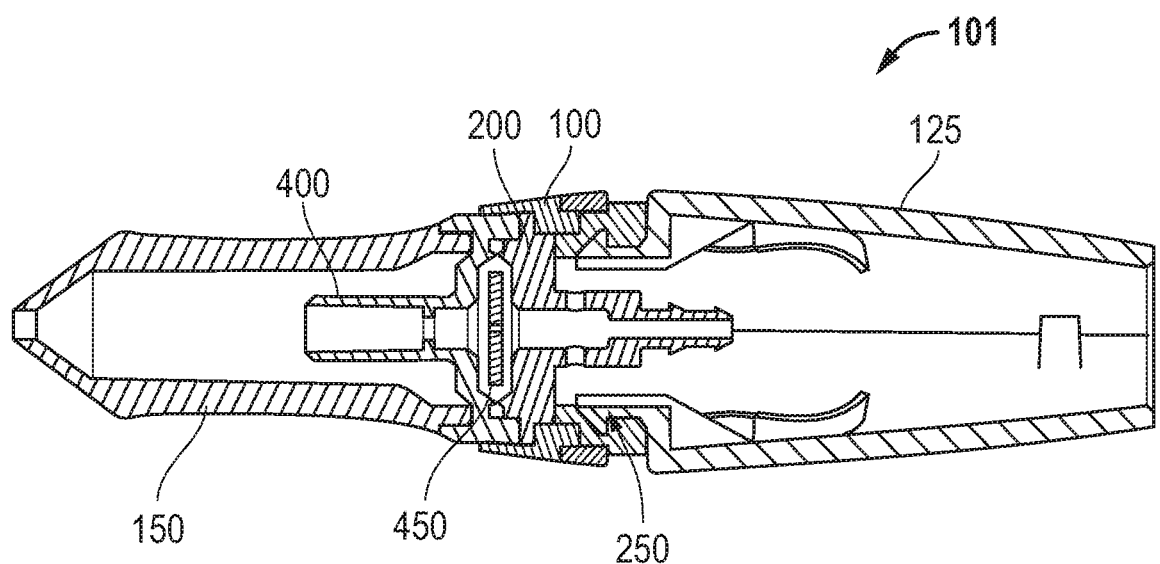
FIG. 4A is a side cross-sectional view of the vitrectomy probe of FIG. 1 revealing internal components.
Figure 4B:
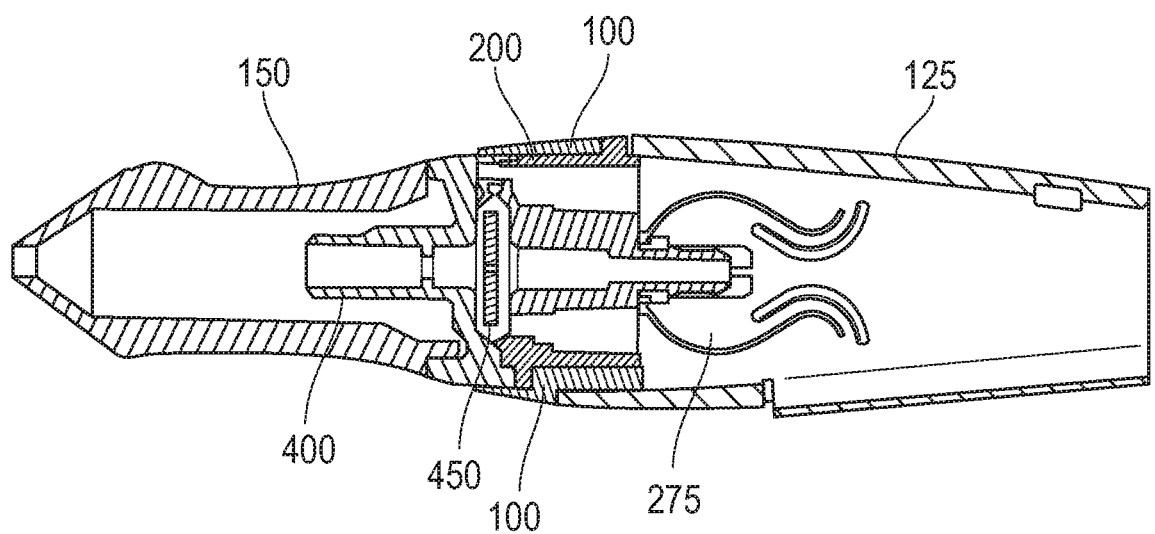
FIG. 4B is a top cross-sectional view of the vitrectomy probe of FIG. 4A, rotated 90° to reveal internal components from another perspective.

Referring now to FIGS. 4A and 4B, cross-sectional views of the vitrectomy probe 101 of FIG. 1 are shown revealing internal components. Specifically, FIG. 4A may be referred to as revealing a top view whereas FIG. 4B is rotated about 90° from the top view to reveal another perspective of the internal components.

Notably, the internal housing 200 accommodates a diaphragm 450 that is reciprocated by an influx of air through channels. This occurs with the air alternatingly being applied to either side of the diaphragm 450 such that the reciprocation takes place. In this way, an extension tube 400 that accommodates the cutter may be reciprocating for cutting of vitreous humor as described above.

Reciprocating of the diaphragm 450 as described means that it will continuously strike structure of the internal housing 200 each time it completes a stroke in one direction or the other. This is the primary reason for the noted vibrations. However, as noted above, the interfacing component 100 is of such architecture and material construction that the majority of these vibrations fail to reach the shell 125 even when left in place during a surgical procedure.

Continuing with reference to FIGS. 4A and 4B, catch extensions 250 are shown. It is at these discrete locations where contact between the internal housing 200 and the shell 125 occurs (see FIG. 4A). The remainder of the shell 125 is kept from direct interface with this housing 200 by the interfacing component 100 (see FIG. 4B).

With specific reference to FIG. 4B, a depressible tab 275 for one of the extensions 250 is visible. Thus, with simultaneous reference to FIG. 4A it is apparent how depressing such extensions 250 inward would result in release of the extensions 250 from engagement with the internal housing 200 for surgeons electing this option.

Figure 5:
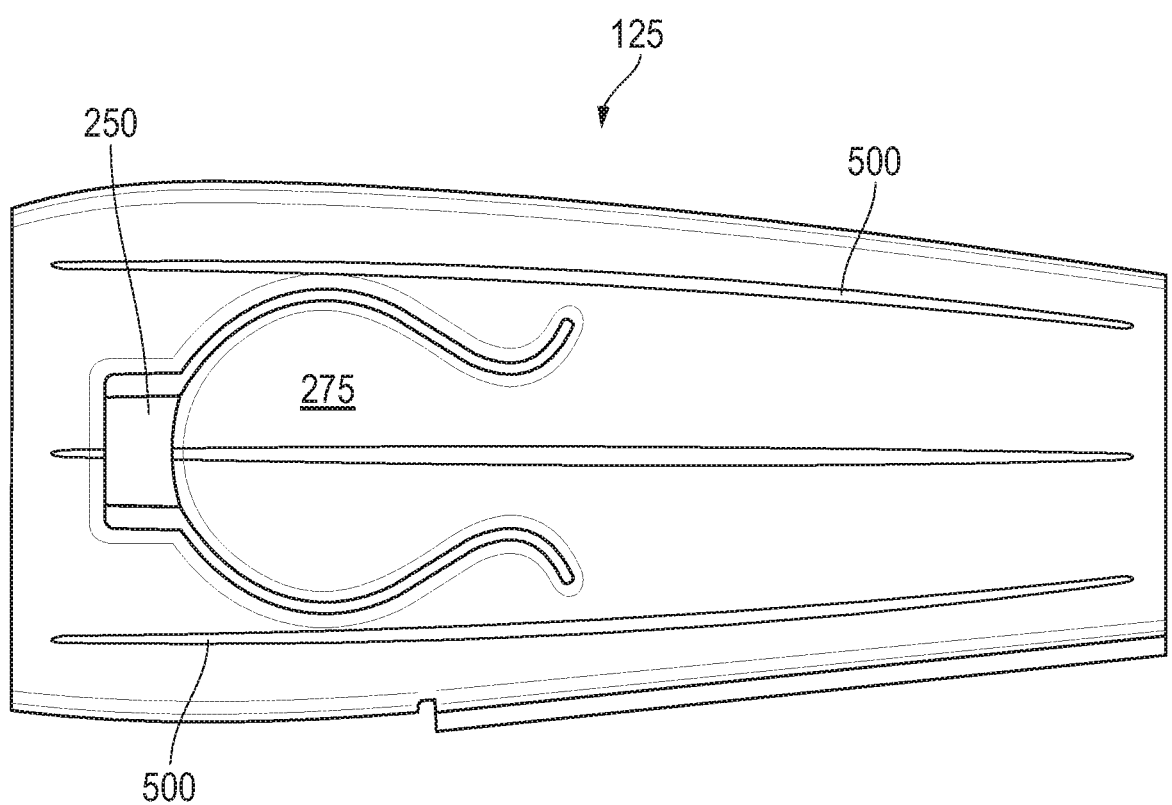
FIG. 5 is an enlarged top view of the shell of FIGS. 1, 2, 4A and 4B, removed from the vitrectomy probe.

Referring now to FIG. 5, an enlarged top view of the shell 125 of FIGS. 1, 2, 4A and 4B, is illustrated. In this view, the depressible tab 275 is apparent with underlying catch extension 250 as described above. Additionally, ergonomic ridges 500 are shown at the surface of the shell 125. These ridges 500 may promote a degree of rest or stillness of the shell 125 at the surgeon's hand during a vitrectomy procedure.

Figure 6:
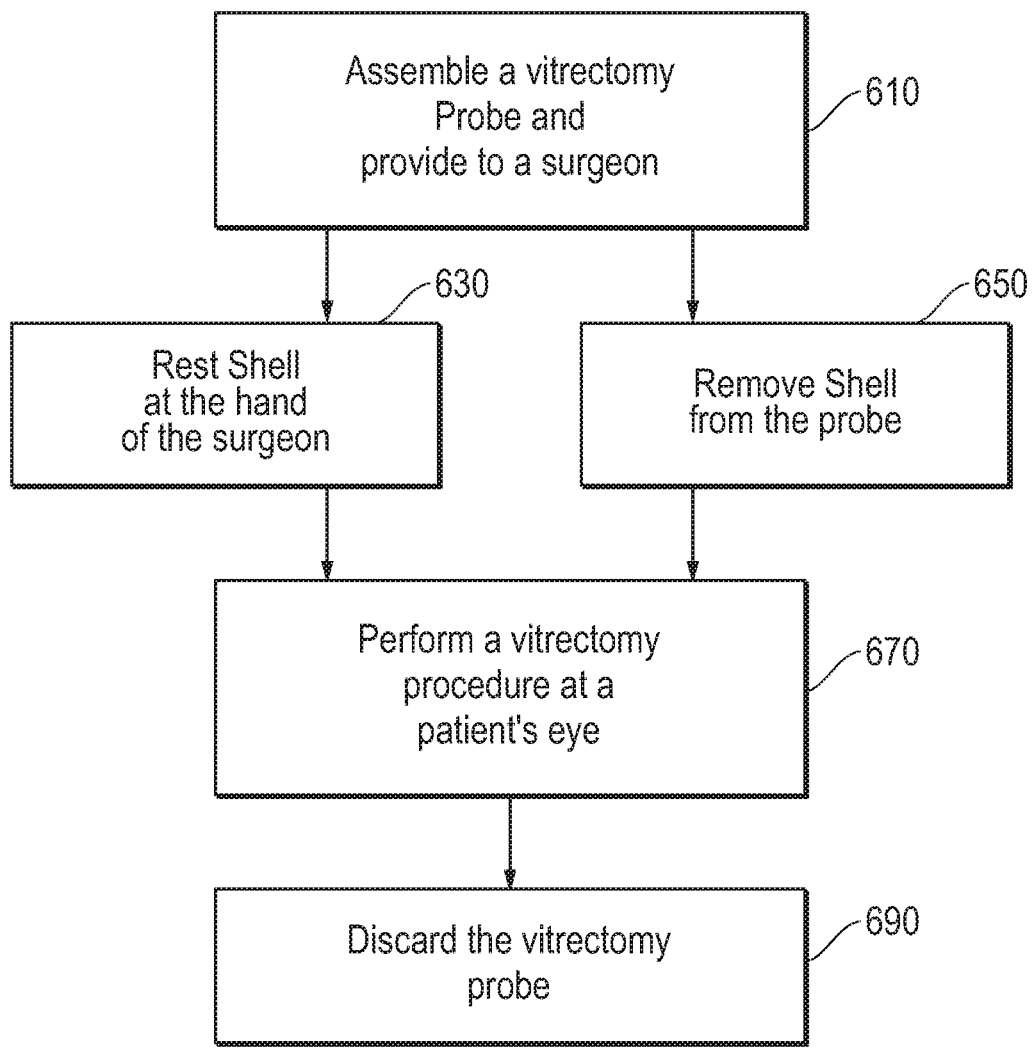
FIG. 6 is a flow-chart summarizing an embodiment of utilizing a vitrectomy probe during a vitrectomy procedure.

Referring now to FIG. 6, a flow-chart summarizing an embodiment of utilizing a vitrectomy probe during a vitrectomy procedure is shown. Namely, an assembled vitrectomy probe is provided as indicated at 610. The surgeon may then remove the shell in a user-friendly manner if desired (see 650). Alternatively, the surgeon may keep the shell on the probe and allow it to rest at the purlicue of the hand as noted at 630. In either case, the vitrectomy may be performed as indicated at 670 with distracting shell vibrations completely or substantially eliminated. Either way, the unique interfacing component of the probe has allowed for this benefit. In the end, the surgeon may complete a less distracting eye surgery and discard the probe as indicated at 690.

Embodiments described hereinabove include a vitrectomy probe with an interfacing component that attenuates potentially distracting vibrations from a surgeon's perspective. Once more, for the surgeon that chooses, the shell may be removed entirely in a user-friendly manner without requiring that the surgeon crudely pry apart the probe.

The preceding description has been presented with reference to presently preferred embodiments. However, other embodiments and/or features of the embodiments disclosed but not detailed hereinabove may be employed. For example, the shell is described as being secured to the internal housing through two discrete catch extension locations. However, in other embodiments more than two such locations may be provided. Alternatively, in other embodiments, the shell may open at a single locations such as a slit running the length of the shell body from the leading edge to the opposite side wherein the slit is held together by a C-clip, I-wedge or even by natural force requiring a prying force to open. Regardless, for such embodiments, the leading edge of the shell may circumferentially squeeze sufficiently against the interfacing component with enough force to stably hold thereat without the need for any physical contact with the internal housing. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

We claim:

1. A vitrectomy probe comprising:
   a component housing for accommodating moving components for supporting a vitrectomy procedure;
   an ergonomic shell for probe support during the procedure; and
   a securing interface accommodating each of the shell and the housing and positioned there between, the interface for mitigating vibrations from reaching the shell during the procedure from the moving components;
   wherein the ergonomic shell is physically coupled to the housing at discrete catch extension locations, the interface substantially eliminating contact between the shell and the housing outside of the extension locations for the mitigating of the vibrations; and
   wherein the shell is removable by deflection of catch extensions of the shell at the locations, and comprising depressible tabs at an exterior surface of the shell to facilitate the deflection.

2. The vitrectomy probe of claim 1 wherein the securing interface is of elastomeric construction for the mitigating of the vibrations.

3. The vitrectomy probe of claim 1 wherein the interfacing component physically interfaces a leading edge of the shell for more than about 300° circumferentially.

4. The vitrectomy probe of claim 1 wherein the discrete locations occupy less than about 75° circumferentially.

5. The vitrectomy probe of claim 1 further comprising ergonomic ridges at an exterior surface of the shell for ergonomic support.

* * * * *